United States Patent [19]

Szabolcs née Borbás et al.

[11] Patent Number: 4,544,740
[45] Date of Patent: Oct. 1, 1985

[54] PROCESS FOR THE PREPARATION OF 5-(2-BROMOVINYL)-URIDINE

[75] Inventors: Anna Szabolcs née Borbás; László Ötvös; János Sági; Attila Szemzö; Mária Peredy née Kajtár; István Horváth; István Koczká; Csilla Rétháti; Pál Iván; Ildikó Fritzsche née Lukács; János Nagy, all of Budapest, Hungary

[73] Assignee: Egyt Gyogyszervegyeszeti Gyar, Budapest, Hungary

[21] Appl. No.: 415,424

[22] Filed: Sep. 7, 1982

[30] Foreign Application Priority Data

Sep. 7, 1981 [HU] Hungary ............... 2571/81

[51] Int. Cl.$^4$ ........................... C07H 19/08
[52] U.S. Cl. ........................... 536/23; 536/122
[58] Field of Search ............ 424/180; 536/23

[56] References Cited

U.S. PATENT DOCUMENTS

| | | | |
|---|---|---|---|
| 4,247,544 | 1/1981 | Bergstrom et al. | 536/23 |
| 4,382,925 | 5/1983 | de Clercq et al. | 536/23 |
| 4,386,076 | 5/1983 | Machida et al. | 536/23 |

FOREIGN PATENT DOCUMENTS

| | | | |
|---|---|---|---|
| 0031128 | 7/1981 | European Pat. Off. | 536/23 |
| 0060099 | 9/1982 | European Pat. Off. | 536/23 |
| 0061283 | 9/1982 | European Pat. Off. | 536/23 |

OTHER PUBLICATIONS

Kulikowski et al., "Jour. of Medicinal Chem.", vol. 17, No. 3, 1974, pp. 269–273.
de Clercq, "Meth. and Find. Exptl. Clin. Pharmacol.", vol. 2, No. 5, pp. 253–267, 1980.
Jones et al., Tetrahedron Letters, No. 45, pp. 4415–4418, 1979.

*Primary Examiner*—Johnnie R. Brown
*Attorney, Agent, or Firm*—Keil & Weinkauf

[57] ABSTRACT

The invention relates to (E)-5-(2-bromovinyl)-uridine and its derivatives of general formula VI,

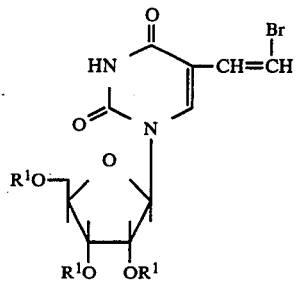

wherein $R^1$ stands for a hydrogen atom, $C_{1-8}$ alkanoyl group, benzoyl group or a benzoyl group substituted in para position either with a $C_{1-4}$ alkyl group or a halogen atom, and a process for preparing them by brominating 2′,3′,5′-tri-O-acyl-5-ethyl-uridine of general formula IV,

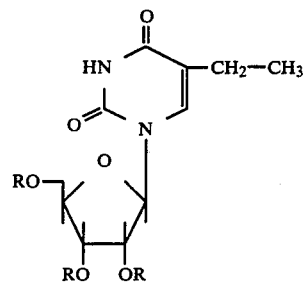

wherein R is identical with $R^1$, except where $R^1$ stands for a hydrogen atom, dehydrohalogenating the resulting dibromo compound of general formula V

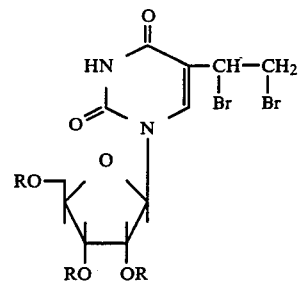

and optionally deacylating it.

The resulting compounds of general formula VI are exhibiting significant potency against Herpes simplex virus species and are of remarkably low acute toxicity.

8 Claims, 6 Drawing Figures

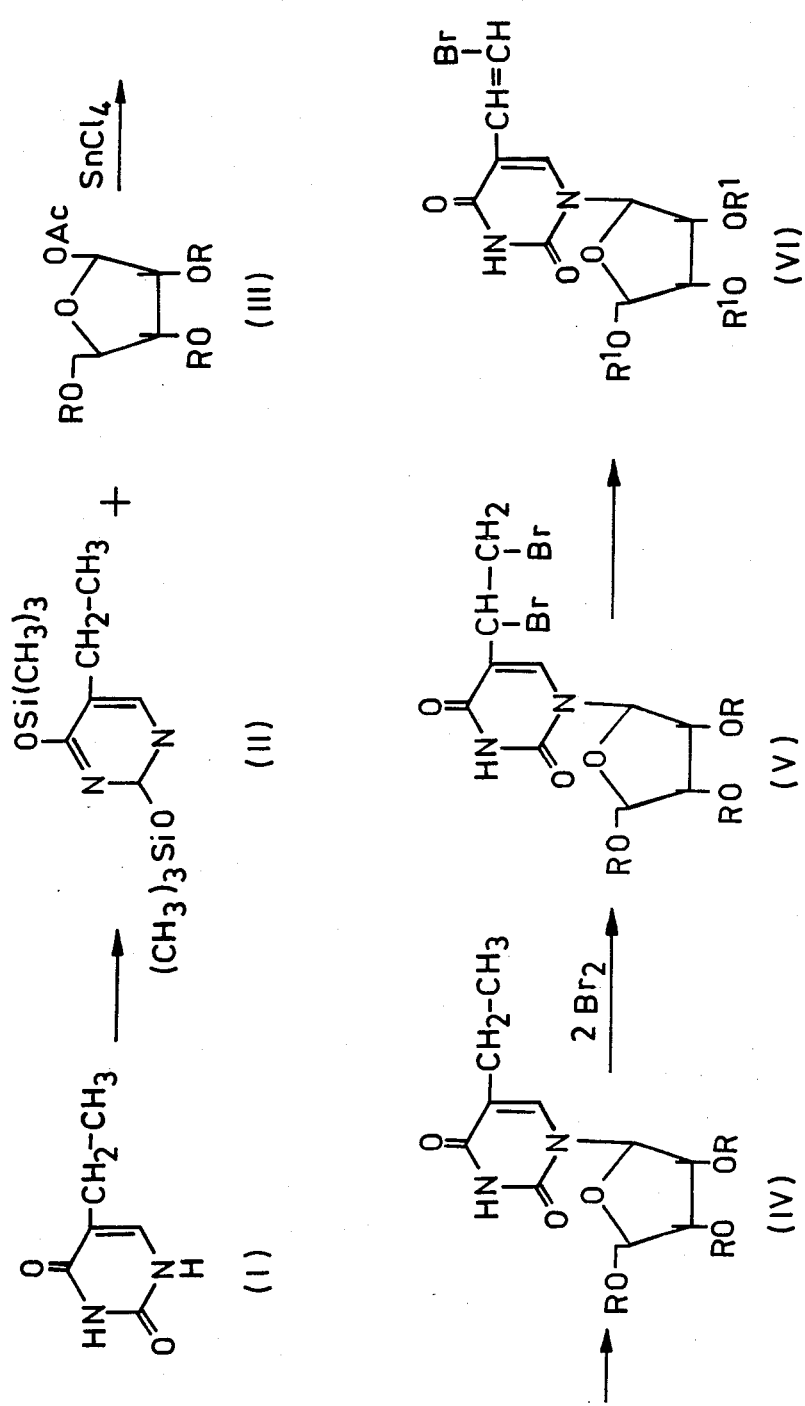

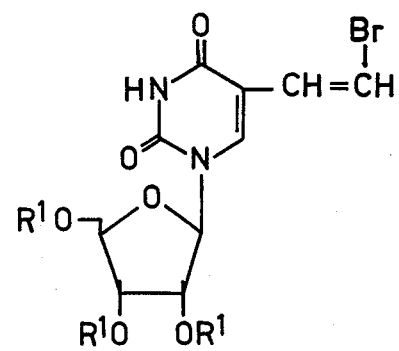
(VI)

PROCESS FOR THE PREPARATION OF 5-(2-BROMOVINYL)-URIDINE

The invention relates to (E)-5-(2-bromovinyl)-uridine and its derivatives of formula VI

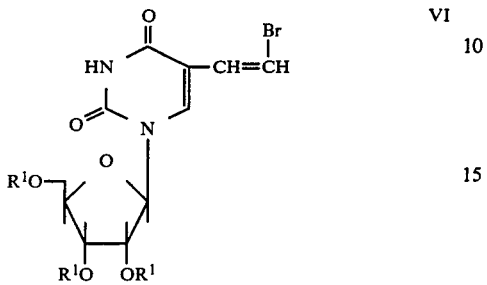

wherein $R^1$ stands for a hydrogen atom, $C_{1-8}$ alkanoyl group, benzoyl group or a benzoyl group substituted in para position either with a $C_{1-4}$ alkyl group or a halogen atom. Furthermore, the invention relates to a process for the preparation of these compounds.

It is known that the 2'-deoxy-nucleosides of the 5-substituted uracil base exhibit, both in vitro and in vivo, significant antiviral activity [Meth. and Find. Exptl. Clin. Pharmacol. 2, 253 (1980)]. Of the known nucleosides the (E)-5-(2-bromovinyl)-uracil-2'-deoxynucleoside possesses marked anti-herpes potency (activity against Herpes simplex virus species) [Proc. Natl. Acad. Sci. USA 76, (6) 2946 (1979)].

It is also known that in the group of pyrimidine nucleosides substituted with a lower alkyl group in position 5 only deoxyribonucleosides are exhibiting anti-herpes activity while the corresponding ribonucleosides remain nearly inactive [Chem. Pharm. Bull 18, 261 (1970)].

Unexpectedly it was found that the ribonucleoside of (E)-5-(2-bromovinyl)-uracil base, prepared instead of the 2'-deoxyribonucleoside, has a similarly high anti-herpes potency while being simultaneously less toxic.

Furthermore, it was found that this novel nucleoside and its derivatives can be prepared advantageously by brominating 2',3',5'-tri-O-acyl-5-ethyl-uridine of general formula IV—wherein R is identical with $R^1$, except when $R^1$ stands for a hydrogen atom—dehydrohalogenating the resulting dibromo compound of general formula V and then optionally deacylating it. The uridine derivatives of general formula IV can be advantageously prepared starting from 5-ethyl-uracil (I) and applying consecutive high yield synthesis steps, through intermediary compounds of general formula II and III, according to the following reaction scheme:

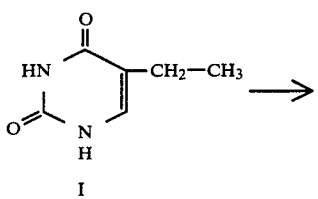

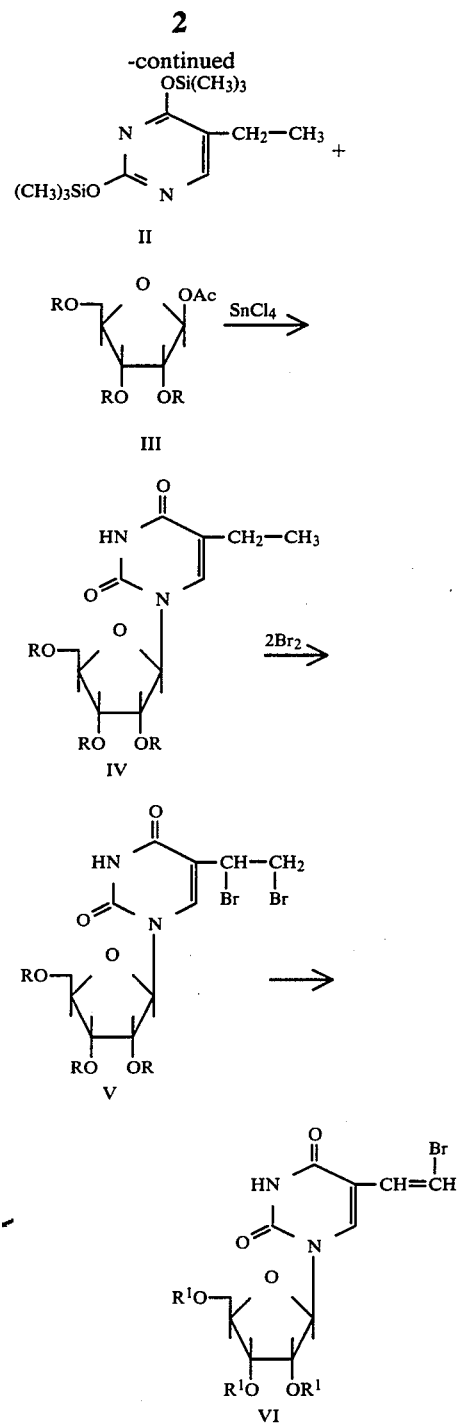

In compliance with the invention (E)-5-(2-bromovinyl)-uridine and its derivatives of general formula VI, wherein R' stands for a hydrogen atom, $C_{1-8}$ alkanoyl group, benzoyl group or a benzoyl group substituted in para position either with a 1 to 4 C-alkyl group or a halogen atom—can be prepared by brominating 2',3',5'-tri-O-acyl-5-ethyl-uridine of formula IV, wherein R stands for a $C_{1-8}$ alkanoyl group, benzoyl group or a benzoyl group substituted in para position with a 1 to 4 C-alkyl group or a halogen atom, with bromine, dehydrohalogenating the resulting dibromo derivative of general formula V wherein R has the same meaning as above and optionally deacylating it.

According to a preferred method of the invention 1M of 2',3',5'-tri-O-acyl-5-ethyl-uridine of the formula IV, preferably dissolved in a halogenated solvent, such as dichloromethan, dichloroethan or carbontetrachloride, is brominated in the presence of UV light with 2,5M of bromine, the resulting dibromo derivative of the formula V is optionally separated, then is dehydrohalogenated in the presence of an excess of a teritary base, preferably triethylamine, in a halogenated solvent or ethyl acetate, and finally is optionally deacylated with an alkali metal lower alcoholate in a lower alkanol.

The antiviral potency of the compounds of general formula VI of the invention is demonstrated by using (E)-5-(2-bromovinyl)-uridine as an example.

The testing of antiviral activity was carried out according to the following considerations:

According to the literature the major part of antiviral nucleoside analogues is presumed to exert its "antiviral potency" by interfering with the functioning of the host cell which as a result fails to promote intracellular virus multiplication (it is a well known fact that virus multiplication requires a well functioning host cell).

A method was developed for the testing of the antiviral activity of various drugs in solution which is suitable for the exact, sensitive and objective in vitro assay of drug activity exerted on the cells and tissues of both warm-blooded animals and men [Toxicology 16, 59 (1980)]. The method is also suitable for calculating from the test data the highest concentration of the test drug in the tissue culture medium which is not impairing the tissue yet ($CT_o$). The antiviral activity of a drug is considered virus-specific, i.e. especially suitable for therapeutic purposes, if it can inhibit virus multiplication in the tissue at concentrations of $CT_o$ or lower than $CT_o$, consequently it may be presumed to have low acute toxicity in warm-blooded animals and men. (Low toxicity is especially advantageous in the case of compounds which are designed to be launched as antiviral drugs).

both compounds exert marked antiviral effect in vitro even at such low concentrations as $CT_o$ without impairing the cells and tissues used for culturing. Unexpectedly, however, (E)-5-(2-bromovinyl)-uridine exerted significantly lower toxicity than the deoxy derivative. The antiviral effect of the compounds is confirmed by the test results summarized in Table 1.

TABLE 1

Effect of nucleoside analogues on virus multiplication in cell cultures at concentrations of $CT_o$

| Compound | Virus strains | | | |
|---|---|---|---|---|
| | Herpes simpl.[1] | Adeno[2] | Rubeola[3] | Influenza[4] |
| A | ++++ | O | O | O |
| B | ++++ | O | O | O |
| C | O | — | — | O |
| D | O | — | — | O |

Abbreviations:
A = (E)-5-(2-bromovinyl)-uridine
B = (E)-5-(2-bromovinyl)-2'-deoxy-uridine
C = 5-iodo-2'-deoxy-uridine
D = 5-iodo-2'-deoxy-cytidine
++++ = significant inhibition of multiplication
O = inactive
— = not tested
[1] = type 1 in HeLa cell culture
[2] = type 5 in Hep-2 cell culture
[3] = Judith strain in Rk-13 cell culture
[4] = AO PRS strain in chorioallantois-membrane culture (E)-5-(2-Bromovinyl)-uridine was found to be very active in inhibiting the multiplication of type 1 Herpes simplex virus. In tissue cultures containing (E)-5-(2-bromovinyl)-uridine in a concentration of $CT_o$, the virus count, measured in $TCID_{50}$ (virus concentration destroying 50 percent of the cell culture), was significantly reduced compared to similar values assayed in the control test tubes devoid of active ingredient. The difference in the logarithm of virus titers may be considered the objective indicator of the rate of inhibition of virus multiplication. The test results of several experiments, containing also comparative data of both (E)-5-(2-bromovinyl)-uridine and (E)-5-(2-bromovinyl)-2'-deoxy-uridine, are summarized in Table 2.

TABLE 2

Inhibitory effect of nucleoside analogues on virus multiplication
Test virus: type 1 Herpes simplex
Cell culture: HeLa (the Eagle solution,[x] prepared from standard Earle solution contained 2 percent of calf serum)
Test results of several individual experiments:

| | Control log $TCID_{50}$ | Compd. A log $TCID_{50}$ | Δ log $TCID_{50}$ | Control log $TCID_{50}$ | Compd. B log $TCID_{50}$ | Δ log $TCID_{50}$ |
|---|---|---|---|---|---|---|
| | 6.0 | 2.77 | 3.23 | 5.83 | 2.5 | 3.33 |
| | 5.83 | 2.5 | 3.33 | 5.5 | 1.66 | 3.84 |
| | 5.75 | 2.5 | 3.25 | 6.0 | 2.22 | 3.78 |
| | 6.0 | 3.0 | 3.0 | 5.83 | 2.66 | 3.17 |
| | 5.66 | 2.5 | 3.16 | | | |
| | 6.0 | 3.0 | 3.0 | | | |
| | 5.5 | 2.33 | 3.17 | | | |
| Average: | 5.82 | 2.66 | 3.16 | 5.79 | 2.26 | 3.53 |

Abbreviations:
Compd. A = (E)-5-(2-bromovinyl)-uridine
Compd. B = (E)-5-(2-bromovinyl)-2'-deoxy-uridine
$TCID_{50}$ = virus concentration destroying 50 percent of the cell culture
[x]H. Eagle: Amino acid metabolism in mammalian cell cultures, Science 130, 432 (1959)

Unfortunately either no similar toxicity data ($CT_o$) are published in the literature about drugs described as "antiviral", or the tests were carried out at concentrations higher than $CT_o$ and these solutions were found to exhibit "antiviral potency". Comparing the antiviral potency of (E)-5-(2-bromovinyl)-uridine with that of the known (E)-5-(2-bromovinyl)-2'-deoxy-uridine [Tetrahedron Letters No. 45, 4415 (1979)] it was found that Deviation in the difference between $TCID_{50}$ 3.16 and 3.53 is rather slight though significant ($p = > 0.05$).

Both (E)-5-(2-bromovinyl)-uridine and (E)-5-(2-bromovinyl)-2'-deoxy-uridine exhibit similar antiviral effect, the deviation between log $TCID_{50}$ differences 3.16 and 3.53 is rather slight.

Compared to the biological effect of other antiviral nucleoside type compounds described in the literature (E)-5-(2-bromovinyl)-uridine proved to be less toxic in our experiments carried out in tissue culture, similarly to our comparative tests with (E)-5-(2-bromovinyl)-2'-deoxy-uridine.

TABLE 3

Cytotoxicity of nucleoside analogues at concentrations of $CT_o$ and $CT_{50}$ in various cell cultures in log μg/ml

| Compound | HeLa | | RK-13 | | BHK-21 | | Vero | |
|---|---|---|---|---|---|---|---|---|
| | $CT_{50}$ | $CT_o$ | $CT_{50}$ | $CT_o$ | $CT_{50}$ | $CT_o$ | $CT_{50}$ | $CT_o$ |
| A | 2.6 | 2.0 | 2.7 | 1.6 | 2.7 | 2.1 | 2.6 | 2.0 |
| B | 2.4 | 1.6 | 2.9 | 1.3 | 2.9 | 2.5 | 2.5 | 1.6 |
| C | 1.3 | −1.4 | 1.9 | 0.7 | 0.8 | −1.0 | 1.6 | 1.5 |
| D | 0.9 | −2.0 | | | | | | |

Abbreviations:
A = (E)-5-(2-bromovinyl)-uridine
B = (E)-5-(2-bromovinyl)-2'-deoxy-uridine
C = 5-iodo-2'-deoxy-uridine
D = 5-iodo-2'-deoxy-cytidine In tests carried out in HeLa cell cultures (E)-5-(2-bromovinyl)-uridine exhibited a therapeutic index of $10^{1.8} = 63$ against Herpes simplex type 1 virus compared to controls exerting 50 percent inhibition.

The favourable tissue toxicity of (E)-5-(2-bromovinyl)-uridine was also confirmed in the course of a simple toxicity trial performed on mice ($LD_{50}$).

TABLE 4

Acute toxicity of (E)-5-(2-bromovinyl)-uridine in mice
Solvent: 20 percent aqueous dimethylsulfoxide

| | | Acute toxicity after a single dose /measured after 24 hours/ | |
|---|---|---|---|
| | Dose | Number of dead/treated animals | |
| Application | mg/kg | A | B |
| i.v. | 300$^x$ | 0/5 | 1/5 |
| i.p. | 1000$^{xx}$ | 4/5 | 5/5 |
| | 750 | 0/5 | 2/5 |
| | 500 | 0/5 | 0/5 |
| per os | 1000$^{xx}$ | 0/5 | 0/5 |
| | 1500$^{xx}$ | 0/5 | 0/5 |

Abbreviations:
A = (E)-5-(2-bromovinyl)-uridine
B = (E)-5-(2-bromovinyl)-2'-deoxy-uridine (reference substance)
$^x$i.v. trial was limited due to poor water solubility of the compound
$^{xx}$aqueous suspension of the compound was used applying polyoxy-ethylen-sorbitol-monooleate (Tween 80) and carboxy-methyl-cellulose On the basis of preliminary trials, injections, ointments and tablets, containing (E)-5-(2-bromovinyl)-uridine as active ingredient and prepared by methods known per se, are suitable both for the specific topical and also for the systemic treatment of human Herpes simplex virus type 1 infections.

The invention is further illustrated by but not limited to the following Examples.

EXAMPLE 1

2',3',5'-Tri-O-benzoyl-(E)-5-(2-bromovinyl)-uridine (VI), $R^1$=benzoyl)

56.0 g (0.095M) of 2',3',5'-tri-O-benzoyl-5-ethyl-uridine are dissolved at moderate heating in 400 ml of anhydrous dichloromethan. The heating is discontinued and 34.15 g (11 ml) of bromine are added within 20 to 25 minutes under nitrogen current, by applying UV irradiation. The UV irradiation is stopped after the bromine addition is completed and the reaction mixture heated under reflux in a strong nitrogen current for 30 to 40 minutes. Then both the solvent and the hydrogen bromide formed are removed at reduced pressure. The residual pale yellow syrup is taken up in 20 ml of anhydrous dichloromethane and the evaporation is repeated. The residue is dissolved in 200 ml of anhydrous ethyl acetate, 15 ml of triethylamine are added drop-wise at constant stirring, the triethylamine hydrobromide formed is filtered, then washed twice with 20 ml of ethyl acetate. The combined ethylacetate washings are evaporated at reduced pressure. The residue is a solid foam, 63.0 g, yield 100 percent. This product may be optionally directly deacylated. The foam can be converted into white crystals, m.p. 160 to 170 C.°, by scratching it with ethanol.

The starting material of this example, 2',3',5'-tri-O-benzoyl-5-ethyl-uridine, can be prepared according to the following reaction route.

a. 2,4-Bis-(O-trimethylsilyl)-5-ethyl-uracil (II)

40 g (0.285 mM) of ethyl-uracil (I), dried prior to the reaction at 150 C.° in vacuo, are mixed with 80 ml (0.50M) of 1,1,1,3,3,3-hexamethyl-di-silasan, and heated under reflux at anhydrous conditions for 24 hours. The clear solution formed is evaporated at atmospheric pressure. The residue is a sticky syrup which is submitted to distillation at reduced pressure. B.p. 134 C.° (1733 Pa). Yield: 78.95 g (97 percent).

b. 1-O-Acetyl-2,3,5-tri-O-benzoyl-D-ribose (III)

60 g (0.4M) of D-ribose are dissolved in 1280 ml of anhydrous methanol, and 34 ml of methanol, saturated with anhydrous hydrochloric acid gas (11.2 percent), are added. The reaction mixture is left for 20 hours at room temperature at anhydrous conditions, then is neutralized with 120 ml of pyridine, and evaporated at reduced pressure at 30 to 40 C.°. This evaporation is repeated following the addition of an other 120 ml portion of pyridine. The resulting viscous, slightly yellow syrup is dissolved in a mixture of 304 ml of pyridine and 320 ml of chloroform, 233.8 ml of freshly distilled benzoyl chloride are added under ice-cooling, and it is left in an ice box overnight. Next day the excess is benzoyl chloride is destroyed by pouring the reaction mixture on ice and separating the aqueous and organic solvent layer. The aqueous phase is extracted twice with 160 ml of chloroform, the combined chloroform extracts are washed with 200 ml of water, dried over anhydrous sodium sulfate and evaporated in vacuo at 30 to 40 C.°. The evaporation is repeated following addition of 100 ml of toluene. The residual red oil, obtained following removal of the last traces of organic solvent, is dissolved in a mixture of 96 ml of glacial acetic acid and 224 ml of acetic anhydride, then 32 ml of 95 to 97 percent sulfuric acid are added to the solution during 2 to 3 hours under ice cooling and vigorous stirring, and the mixture is left to stand overnight in the refrigerator. Next day the solution is poured onto ice, and the water is decanted from the oily crystals formed. The crystals are stirred with 500 ml of water, the water repeatedly decanted, the crystals are stirred with 200 ml of a 50 to 80 percent aqueous methanol and filtered. The crude product is recrystallized from 2.5 L of methanol. Yield: 128.5 g (60.0 percent) of 1-O-acetyl-2,3,5-tri-O-benzoyl-D-ribose, m.p. 131 C.°.

c. 2',3',5'-Tri-O-benzoyl-5-ethyl-uridine (IV)

48.1 g (0.095M) of 1-O-acetyl-2,3,5-tri-O-benzoyl-D-ribose (III) are dissolved in 1690 ml of dichloromethane and a mixture of 33.7 g (0.118M) of 2,4-bis-(O-trimethyl-silyl)-5-ethyl-uracil (II) and 14 ml of tin (IV) chloride in 110 ml of dichloromethane are added at constant stirring. Following agitation for 2 to 3 hours, the reaction mixture is left to stand for 24 hours at room temperature, then it is extracted with 2300 ml of a saturated, aqueous solution of potassium-hydrogen-carbonate, the organic layer is separated and evaporated at reduced pressure. The residue, a white crystalline material, is recrystallized from 250 ml of ethanol. Yield: 53.5 g (95 percent) of 2',3',5'-tri-O-benzoyl-5-ethyl-uridine (IV), m.p. 155 to 156 C.°.

Applying the process described in Example 1 the following compounds of general formula VI are prepared:

| Example No. | Product | M.p. C° |
| --- | --- | --- |
| 2 | 2',3',5'-tri-O-acetyl-(E)-5-(2-bromovinyl)-uridine | 145.5 |
| 3 | 2',3',5'-tri-O-(p-chlorobenzoyl)-(E)-5-(2-bromovinyl)-uridine | 187–188 |
| 4 | 2',3', 5'-tri-O-octanoyl-(E)-5-(2-bromovinyl)-uridine | B.p.: 98–105 133.3 Pa |
| 5 | 2',3', 5'-tri-O-(p-methyl-benzoyl)-(E)-5-(2-bromovinyl)-uridine | 209 |

The starting materials used in the Examples 2, 3, 4, and 5 are prepared similarly to 2',3',5'-tri-O-benzoyl-5-ethyl-uridine (see Example 1).

EXAMPLE 6

(E)-5-(2-Bromovinyl)-uridine (VI, $R^1$=H)

65.5 g (0.11M) of 2',3',5'-tri-O-benzoyl-(E)-5-(2-bromovinyl)-uridine (crude product of Example 1) are deacylated with a mixture of 250 ml of 0.5N sodium methylate and 250 ml of anhydrous methanol, by stirring the reaction mixture for 3 hours at room temperature. Any precipitate, formed eventually, is removed by filtration. The pH of the clear solution is adjusted to 5 to 6 with ion-exchange resin Dowex 50 H+, the resin is filtered off and washed twice with 100 ml of methanol. The combined methanol solutions are evaporated at reduced pressure. The residue is taken up in ethanol and benzene, and the evaporation is repeated. Working up the residue with ether resulted in 33 g of a crude product which is recrystallized first from water, then from ethanol. Yield: 28 g (71.7 percent) of (E)-5-(2-bromovinyl)-uridine (VI, $R^1$=H), m.p. 165 to 167 C.°.

What we claim is:

1. A process for the preparation of (E)-5-(2-bromovinyl)-uridine and its derivatives of formula VI,

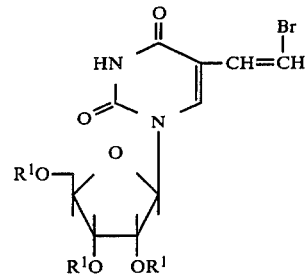

wherein $R^1$ stands for hydrogen, $C_{1-8}$ alkanoyl, benzoyl or benzoyl substituted in the para position either with $C_{1-4}$ alkyl or halogen, by brominating 2',3',5'-tri-O-acyl-5-ethyl-uridine of formula IV,

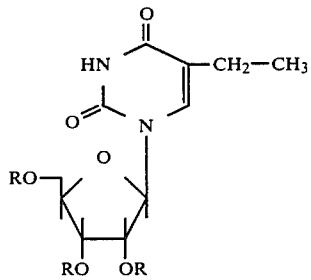

wherein R is identical with $R^1$ as defined above, except where $R^1$ stands for a hydrogen atom, with bromine,—dehydrohalogenating the resulting dibromo compound of formula V,

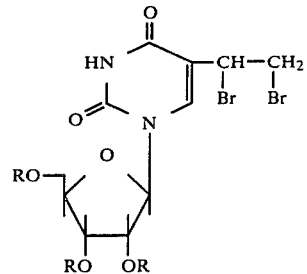

wherein R is identical with $R^1$ as defined above, except where $R^1$ stands for hydrogen.

2. The process of claim 1, which comprises carrying out bromination in a halogenated solvent, in the presence of UV light.

3. The process of claim 1 or 2, which comprises dehydrohalogenating the dibromo derivatives of formula V with a tertiary base.

4. The process as claimed in claim 3, which comprises carrying out dehydrohalogenation in ethyl acetate or a chlorinated solvent.

5. The process of claim 1, which comprises deacylating the end product with an alkali metal lower alcoholate in a lower alkanol.

6. The process of claim 3, wherein the tertiary base is triethylamine.

7. The process of claim 4, wherein the solvent is dichloromethane.

8. The process of claim 1, wherein the end product is deacylated.

* * * * *